United States Patent [19]
Bender et al.

[11] Patent Number: 4,477,668
[45] Date of Patent: Oct. 16, 1984

[54] PROCESS FOR 5-METHYL-10,11-DIHYDRO-5H-DIBENZO[A,D]-CYCLOHEPTEN-5,10-IMINE

[75] Inventors: Dean R. Bender, Hazlet; Sandor Karady, Mountainside; Theresa Rothauser, Clark, all of N.J.

[73] Assignee: Merck & Co., Inc., Rahway, N.J.

[21] Appl. No.: 414,739

[22] Filed: Sep. 3, 1982

Related U.S. Application Data

[63] Continuation-in-part of Ser. No. 366,252, Apr. 7, 1982, abandoned.

[51] Int. Cl.$^3$ ............................................. C07D 471/08
[52] U.S. Cl. ............................................. 546/72; 546/203; 548/528; 568/323; 568/326; 568/808; 564/151; 564/300; 564/308; 564/310; 260/349
[58] Field of Search .......................................... 546/72

[56] References Cited

U.S. PATENT DOCUMENTS 3,717,641 2/1973 Kocsis et al. ........................... 546/72
4,232,158 11/1980 Shepard et al. ........................ 546/72

FOREIGN PATENT DOCUMENTS

78/5291 8/1980 South Africa .
2004872 4/1979 United Kingdom .
2061947 5/1981 United Kingdom .

OTHER PUBLICATIONS

Marched, *Advanced Organic Chemistry*, 2nd ed., (1977), p. 836.
Christy et al., *J. Org. Chem.*, 44, 3117–3127 (1979).
Evans et al., *J. Org. Chem.*, 44, 3127–3135 (1979).
Evans et al., *J. Org. Chem.* 46, 140–143 (1981).
House et al., *J. Org. Chem.* 41, 855–869 (1976).

Primary Examiner—Donald G. Daus
Assistant Examiner—William A. Teoli, Jr.
Attorney, Agent, or Firm—William H. Nicholson

[57] ABSTRACT

(+)-5-Methyl-10,11-dihydro-5H-dibenzo[a,d]-cyclohepten-5,10-imine, and its pharmaceutically acceptable salts is useful as an anxiolytic, antidepressant, anticonvulsant, muscle relaxant and in the treatment of mixed anxiety-depression, minimal brain dysfunction and extrapyramidal disorders such as Parkinson's disease. The racemate of the compound is produced by a four-step synthetic process in about 65% yield from 5H-dibenzo[a,d]cyclohepten-5-one.

9 Claims, No Drawings

PROCESS FOR 5-METHYL-10,11-DIHYDRO-5H-DIBENZO[A,D]-CYCLOHEPTEN-5,10-IMINE

This is a continuation-in-part of Ser. No. 366,252, filed Apr. 7, 1982, now abandoned.

BACKGROUND OF THE INVENTION

This invention is concerned with a novel process for 5-methyl-10,11-dihydro-5H-dibenzo-[a,d]cyclohepten-5,10-imine, and its pharmaceutically acceptable salts which is useful as an anxiolytic, antidepressant, anticonvulsant, muscle relaxant, and in the treatment of mixed anxiety-depression, minimal brain dysfunction and extrapyramidal disorders such as Parkinson's disease.

The product of the novel process of this invention, 5-methyl-10,11-dihydro-5H-dibenzo[a,d]cyclohepten-5,10-imine and its enantiomers are known in the prior art such as Christy et al., J. Org. Chem.; 44, 3117–3127 (1979), South African Pat. No. 78/5291 and its West German counterpart Offenlegungschrift 28 40786. The best process known for synthesis of the racemate consists of nine steps from 5-H-dibenzo[a,d]cyclohepten-5-one with an overall yield of about 23%. Another process disclosed in EP published Application 0019866 prepares the compound in 5 steps with an overall yield of about 4% of theoretical.

Now, with the present invention, there is provided a novel process consisting of four steps from 5H-dibenzo[a,d]cyclohepten-5-one with an overall yield of about 64%.

DETAILED DESCRIPTION OF THE INVENTION

The novel process of the present invention is illustrated by the following Flow Sheet 1:

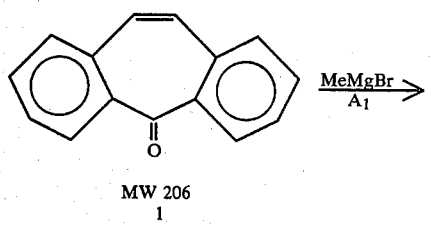

MW 206
1

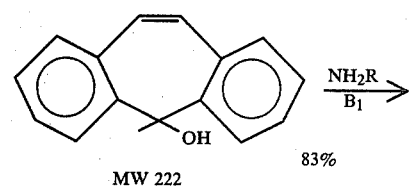

MW 222
2

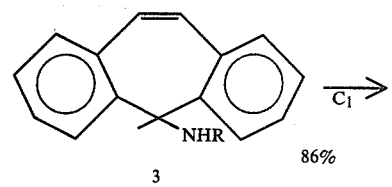

3
86%

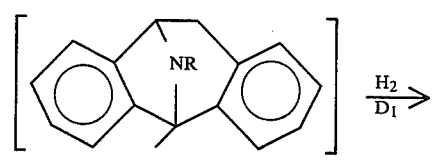

4

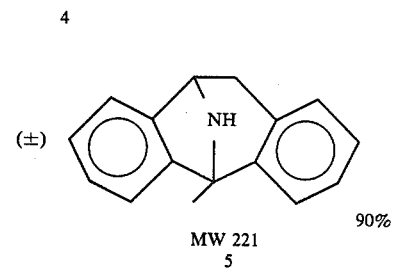

(±)

MW 221
5
90% wherein R is $-OR^1$ wherein $R^1$ is hydrogen or $C_{1-3}$alkyl, or $-NR^2R^3$ wherein $R^2$ and $R^3$ are independently hydrogen, $C_{1-3}$alkyl, $C_{2-3}$alkanoyl, or benzenoid aroyl such as benzoyl or toluyl; or $R^2$ and $R^3$ taken together represent tetramethylene or pentamethylene.

It is preferred that R be $-OH$, $-OCH_3$, $-NH_2$ or $NH-COC_6H_5$, and even more preferred that it be $-OH$.

An alternate procedure is illustrated by the following Flow Sheet 2:

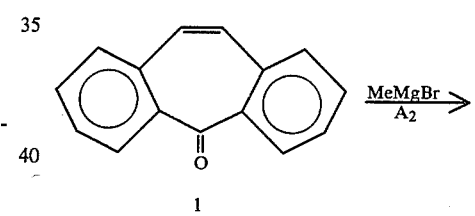

1

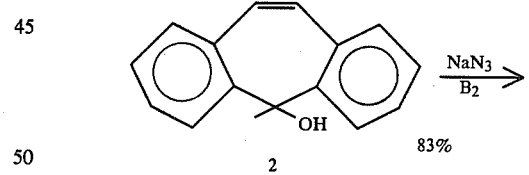

2
83%

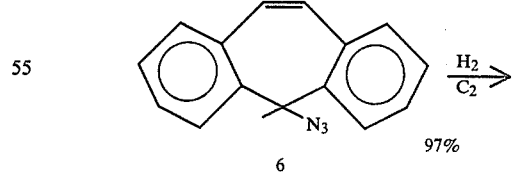

6
97%

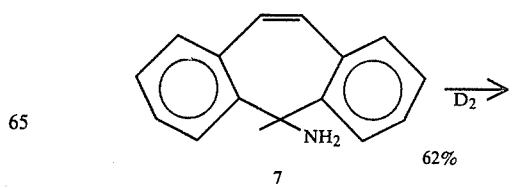

7
62%

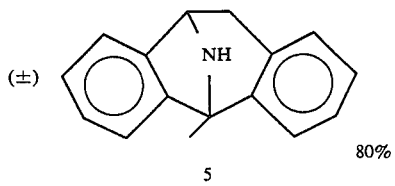

(±)  5  80%

REAGENTS AND CONDITIONS

Steps $A_1$ and $A_2$:
is a Grignard reaction with methylmagnesium halide, preferably the bromide, in an ethereal solvent such as diethyl ether, tetrahydrofuran, 1,2-dimethoxyethane, or the like. The reaction is conducted at $-50°$ C. to about $+50°$ C., preferably at about $15°$–$25°$ C. until the reaction is substantially complete; about 1–2 hours at $15°$–$20°$ C. Aging the reaction for much longer periods such as up to about 24 hours is not deleterious.

Steps $B_1$, and $B_2$:
formation of the substituted amino compound 3, comprises treating a mixture of the substituted amine, and an intermediate strength organic acid such as dichloroacetic acid, trichloroacetic acid, difluoroacetic acid, or the like, or with a mixture thereof, or, in the case of Step $B_2$, with a stronger organic acid such as trifluoroacetic acid in an inert organic solvent such as a chlorinated $C_{1-3}$ alkane, for example methylene chloride, 1,2-dichloroethane, chloroform or the like, with the carbinol 2, at about $-20°$ to $+50°$ C., preferably at about $15°$–$25°$ C. until the reaction is substantially complete. The reaction proceeds rapidly being complete in about an hour.

Steps $C_1$, and $D_2$:
the cyclization, comprises addition of the substituted amino compound, 3, to a strong base such as an alkali metal hydride, amide or alkoxide, especially potassium tert-butoxide, in a solvent system composed of a benzenoid aromatic solvent such as toluene, benzene or the like, dimethylformamide, dimethylsulfoxide or mixtures thereof at about $0°$ to about $190°$ C., preferably about $50°$ to $125°$ C. until the reaction is substantially complete. Times of up to 20 hrs. or longer may be employed.

Alternatively, in the case of Step $C_1$, the cyclization is conducted with no strong base, merely by heating the substituted amino compound in similar solvent systems above about $100°$ C. until the ring closure is substantially complete, in about 10 to 20 hours. Refluxing toluene is preferred. The cyclization is preferably conducted in an inert atmosphere, such as under nitrogen.

Steps $D_1$, and $C_2$:
is the hydrogenolysis of the N-R group which comprises catalytic hydrogenation with a noble metal catalyst such as palladium on carbon, platinum on carbon, platinum oxide, Raney nickel or the like, preferably 5% palladium on carbon, in a solvent such as acetic acid or ethanol or mixtures thereof, with or without a strong mineral acid such as hydrochloric acid, sulfuric acid, phosphoric acid or the like at about $20°$–$100°$ C., preferably about $60°$ C. Hydrogenation is continued until the rate of hydrogen uptake substantially slows and the amount consumed is approximately theoretical.

The product of the novel process of this invention is a racemic mixture, resolvable into its enantiomers by standard techniques such as the formation of diastereomeric salts with an optically active acid, such as (−)-di-p-toluoyl-d-tartaric acid and/or (+)-di-p-toluoyl-l-tartaric acid followed by fractional crystallization and regeneration of the free base.

The product of the novel process of this invention and its dextrorotatory enantiomer are capable of producing anxiety relief without causing excessive sedation or sleep at a dosage level of from about 0.01 to about 20 mg. per kilogram of body weight preferably about 0.05–2 mg/kg of body weight on a regimen of 1–4 times a day. In addition, the product of the process of the present invention and the dextrorotatory enantiomer are useful as antidepressants, muscle relaxants, anticonvulsants and in the treatment of mixed anxiety-depression, minimal brain dysfunction and extrapyramidal disorders, such as Parkinson's disease, when indicated, at comparable dosage levels. It is understood that the exact treatment level will depend upon the case history of the animal or human individual being treated and in the last analysis the precise treatment level falling within the above guidelines is left to the discretion of the therapist.

EXAMPLE 1

Step A:
5-Methyl-5H—dibenzo[a,d]cyclohepten-5-ol (2)

| Materials: | | |
|---|---|---|
| 5H—Dibenzo[a,d]cyclohepten-5-one (1), "trienone" | 875.5 g | 4.25 mol |
| Methylmagnesium bromide 2.28 M in diethylether | 711 g | 5.96 mol |
| Ammonium chloride 5.0 M | 954 g | 17.84 mol |
| Tetrahydrofuran (sieve dried) | 3.79 l. | |
| Hexane | 12 l. | |
| Ethyl acetate | 5.65 l. | |

To, 1.42 l. of dry THF was added with cooling ($T_i$ $5°$–$10°$ C.), 5.96 mol (2.28M in diethylether, 711 g) of methylmagnesium bromide. A solution of 875.5 g (4.25 mol) of "trienone" (1) in 2.37 l. dry THF was then added over a 1.75 hour period to the above mixture, maintaining the temperature between $15°$–$20°$ C. The reaction mixture was brought to room temperature and was then stirred overnight.

The reaction mixture was cooled and an aqueous solution of 5.0M ammonium chloride (954 g, 17.85 mol) was slowly added keeping the temperature at less than $30°$ C.

The organic layer was separated and the aqueous layer, to which NaCl was added, was washed with 3×1.8 l. ethyl acetate.

The organic layers were combined, dried over $Na_2SO_4$, filtered and concentrated under reduced pressure to approximately 1.75 l. (slurry). To this was added 0.25 l. ethyl acetate, which was warmed redissolving all solids. The solution was then cooled to less than $50°$ C. and 10 l. of hexane were added in portions, forming a white fluffy precipitate. This was further chilled ($0°$ to $5°$ C.) for approximately ½ hour. The precipitate was filtered and washed with 2×1 l. cold hexane ($0°$ to $5°$ C.), and air dried at 50°–55° C., to give 783 g (83%) of 2, as a white crystalline solid, m.p. 113.5°–115° C.

Step B:
5-Methyl-5-hydroxamino-5H—dibenzo[a,d]cycloheptene (3)

| Materials: | | |
|---|---|---|
| 5-Methyl-5H—dibenzo[a,d]-cyclohepten-5-ol (2) | 60.0 g | 0.270 mol |
| Dichloroacetic acid | 0.138 l | 1.617 mol |
| Hydroxylamine hydrochloride | 75.11 g | 1.081 mol |
| Sodium acetate | 88.61 g | 1.081 mol |
| Methylene chloride | 2.5 l. | |
| Hexane | 0.8 l. | |
| Concentrated ammonium hydroxide | 0.3 l. | |

To a mixture of 0.138 l. CH$_2$Cl$_2$ and 0.138 l. (1.617 mol) of dichloroacetic acid was added with cooling (T$_i$ 20° C.) 88.61 g (1.081 mol) of sodium acetate. After dissolving the sodium acetate, 75.11 g (1.081 mol) of hydroxylamine hydrochloride was added. The slurry was stirred for 1.5 hours at room temperature and an additional 1.362 l. of CH$_2$Cl$_2$ was added over approximately 10 minutes.

The reaction mixture was then stirred over an additional 1.5 hour period. A solution of 60.0 g (0.270 mol) of the alcohol 2 in 0.600 l. was added to the above reaction mixture over 10 minutes. The reaction was complete after 0.5 hours.

The reaction mixture was quenched with 0.9 l. ice water and 0.3 l. concentrated NH$_4$OH (pH ~ 8).

After stirring, the separated aqueous layer was washed with 1×0.4 l. CH$_2$Cl$_2$, the organic layers combined, washed with 1×0.8 l. brine and dried over Na$_2$SO$_4$. The reaction mixture was filtered and concentrated under reduced pressure to approximately 0.10 l. To this was added in portions with stirring 1.1 l. hexane, forming a white precipitate. This was chilled (0° to 5° C.) for 1 hour, filtered, washed with 0.15 l. cold hexane (0° to 5° C.) and air dried at ambient temperature to give 54.8 g (86%) of 3, a white crystalline solid, which was stored at less than 0° C., m.p. 130°–133° C.

Employing the procedure substantially as described in Example 1, Step B, but substituting for the hydroxylamine hydrochloride used therein, equimolecular amounts of amines of formula NH$_2$R identified in Table I, there were produced the 5-methyl-5-(R-amino)-5H-dibenzo[a,d]cycloheptenes also described in Table I, in accordance with the following reaction scheme:

TABLE I

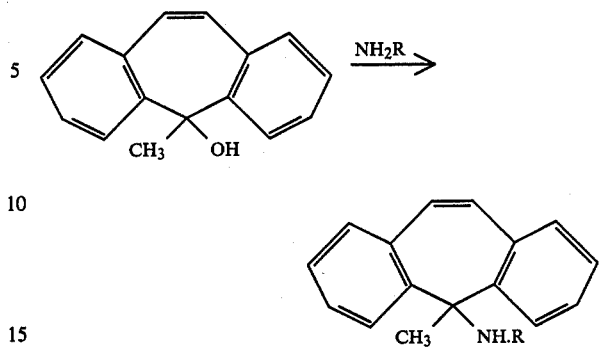

| R | % Yield | Product m.p. (°C.) |
|---|---|---|
| —NH$_2$ | 100 | oil$^{(1)}$ |
| —OCH$_3$ | 82 | 118.5–126 |
| —NHCOC$_6$H$_5$ | 93 | oil$^{(2)}$ |

$^{(1)}$NMR (CDCl$_3$)δ: 2.05(s, 3H, CH$_3$), 3.0(s, 3H, NHNH$_2$), 6.95(s, 2H, —CH=), 7–7.6(m, 8H, aromatic).
$^{(2)}$NMR (CDCl$_3$)δ: 2.15(s, 3H, CH$_3$), 7.1(s, 2H, HC=), 7–7.5(m, 8H, aromatic).

Step C:
12-Hydroxy-5-methyl-10,11-dihydro-5H—dibenzo[a,d]-cyclo-hepten-5,10-imine. (4)

| Materials | | |
|---|---|---|
| 5-Methyl-5-hydroxamino-5H—dibenzo[a,d]cycloheptene (3) | 10.00 g | 0.0422 mol |
| Potassium tert-butoxide | 4.76 g | 0.0422 mol |
| 10% Dimethyl sulfoxide/toluene (sieve dried, v/v) | 100 ml | |
| Toluene | 25 ml | |
| 1:1 (v/v) 1.2 M HCl/glacial acetic acid | 100 ml | |
| Darko KB charcoal | 1.0 g | |

A mixture of 50 ml of 10% DMSO/toluene (sieve dried, v/v) and 4.76 g (0.0422 mol) of potassium tert-butoxide was heated to 55° C. and a solution of 10.00 g (0.0422 mol) of hydroxylamine 3 in 50 ml 10% DMSO/toluene was added quickly and rinsed in with 5 ml toluene.

Three minutes after the addition was complete the reaction mixture was removed from the heat and 50 ml of water added. The reaction mixture was allowed to stir until it reached ambient temperature.

The aqueous layer was separated and back-washed with 20 ml toluene to which 5 ml brine was added. The organic layer was washed with 3×50 ml water and 1×50 ml brine. Each successive aqueous and final brine layer was also back-washed with the 20 ml of toluene. An additional 5 ml of brine was added to the aqueous layers.

The two organic layers were combined, allowed to settle (any additional brine solution remaining was separated) and washed with a 1:1 solution of 1.2M HCl(v/v)/glacial acetic acid, 3×33.3 ml. The acid layers were combined 1.0 g decolorizing charcoal added and the mixture stirred 0.5 hours at ambient temperature. This mixture after filtration, was used in the subsequent hydrogenolysis.

Crystalline ring closed hydroxylamine 5 can be isolated at this point by basification of the concentrated acid layer (NH$_4$OH), extraction (CH$_2$Cl$_2$) and crystallization using a minimum amount of hot CH$_2$Cl$_2$ and hexane (1:8 ratio respectively) to give 12-hydroxy-5-methyl-5H-10,11-dihydro[a,d]cyclohepten-5,10-imine (5) existing as two isomers with combined m.p. 138°–141° C.

Employing the procedure substantially as described in Example 1, Step C, but substituting for the 5-methyl-5-hydroxamino-5H-dibenzo[a,d]cycloheptene used therein, equimolecular amounts of the 5-methyl-5-(R-amino)-5H-dibenzo[a,d]cycloheptenes described in Table II, there were produced the 12-R-5-methyl-10,11-dihydro-5H-dibenzo[a,d]cyclohepten-5,10-imines also described in Table II, in accordance with the following reaction scheme:

TABLE II

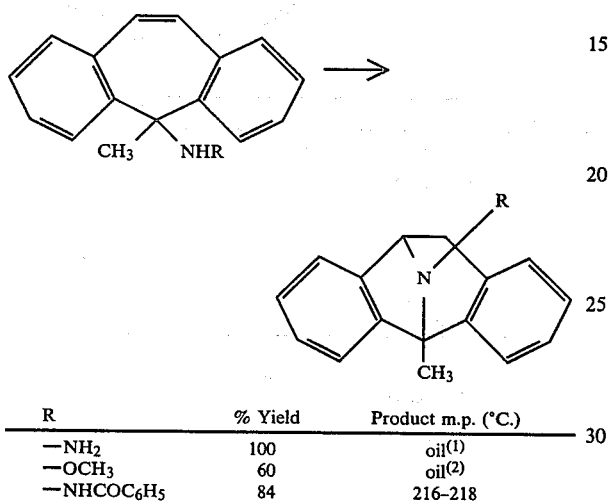

| R | % Yield | Product m.p. (°C.) |
|---|---|---|
| —NH$_2$ | 100 | oil[1] |
| —OCH$_3$ | 60 | oil[2] |
| —NHCOC$_6$H$_5$ | 84 | 216–218 |

[1]NMR (CDCl$_3$)δ: 1.7(s, 3H, CH$_3$), 2.55(d, 1H, J = 17 Hz, —CH$_2$—CH—), 3.45(d of d, 1H, J = 6 and 17 Hz, —CH$_2$—CH), 4.35(d, 1H, J = 6 Hz, —CH—CH$_2$—).
[2]NMR (CDCl$_3$)δ: 1.85 and 1.90(s, 3H, CH$_3$), 2.7(d, 1H, J = 18 Hz, CH$_2$—CH), 3.3(m, partially visible CH$_2$—CH), 3.55(s, 3H, OCH$_3$), 4.6(d, 1H, J = 6 Hz, CH—CH$_2$).

| Alternate Step C: | | |
|---|---|---|
| 12-Hydroxy-5-methyl-10,11-dihydro-5H—dibenzo[a,d]cyclohepten-5,10-imine. (4) | | |
| Materials | | |
| 5-Methyl-5-hydroxamino-5H—dibenzo[a,d]cycloheptene (3) | 2.37 g | 0.01 mol |
| Toluene | 200 ml | |

The mixture of hydroxamino compound and toluene was refluxed 12 hours. The mixture was concentrated to 90 ml in vacuo, and extracted with 3×50 ml of 2N HCl. The extract was adjusted to pH 10 with NH$_4$OH and extracted with 90 ml CH$_2$Cl$_2$. The extract was dried over MgSO$_4$, filtered and concentrated to dryness to give the subject compound in approximately 60% yield.

| Step D: | | |
|---|---|---|
| (±)-5-Methyl-10,11-dihydro-5H—dibenzo[a,d]cyclohepten-5,10-imine | | |
| Materials: | | |
| 12-Hydroxy-5-methyl-10,11-dihydro-5H—dibenzo[a,d]cyclohepten-5,10-imine as a solution in 100 ml of 1:1 (v/v) 1.2 M HCl/glacial acetic acid). | 10.00 g | 0.0422 mol |
| 1:1 (v/v) 1.2 M HCl/glacial acetic acid | 50 ml | |
| Sodium acetate | 5.4 g | 0.061 mol |

| Step D: | | |
|---|---|---|
| (±)-5-Methyl-10,11-dihydro-5H—dibenzo[a,d]cyclohepten-5,10-imine | | |
| 5% Palladium-on-carbon (Engelhard) | 1.0 g | |
| Concentrated ammonium hydroxide | 55 ml | |
| Methylene chloride | 150 ml | |

The mixture of 10.00 g (0.0422 mol; based on 100% yield over the previous step) of the ring closed hydroxylamine 4 and 1.0 g of decolorizing charcoal in 100 ml of 1:1 (v/v) 1.2M HCl/glacial acetic acid was filtered through diatomaceous earth into a 250 ml Parr bottle. The cake was rinsed with approximately 15–25 ml of the HCl/glacial acetic acid mixture until the total volume of the reaction solution was 120 ml.

To this solution was added with warming 5.4 g (0.061 mol) of sodium acetate and 1.0 g of 5% palladium-on-carbon. The mixture was shaken under pressure at 60° C. on the Parr apparatus until the rate of hydrogen uptake clearly slowed.

After approximately 3.25 hours the reaction mixture was degassed with N$_2$, filtered through diatomaceous earth and rinsed with 25 ml of 1:1 (v/v) 1.2M HCl/glacial acetic acid. The reaction was concentrated under reduced pressure to one-half its original volume, 100 ml of ice added, the reaction mixture made basic (pH=8) with concentrated ammonium hydroxide (55 ml) and the basic solution extracted 3×50 ml with CH$_2$Cl$_2$. The organic layers were combined, washed with 1×50 ml brine, dried over Na$_2$SO$_4$, filtered and the solvent concentrated under reduced pressure to give 8.4 g (90%) of 5, a yellow oil which crystallized upon standing, m.p. 77°–85° C.

Employing the procedure substantially as described in Example 1, Step D, but substituting for the 12-hydroxy-5-methyl-10,11-dihydro-5H-dibenzo[a,d]cyclohepten-5,10-imine used therein, equimolecular amounts of the 12-R-5-methyl-10,11-dihydro-5H-dibenzo[a,d]cyclohepten-5,10-imines wherein R is —NH$_2$, —OCH$_3$ and —NHCOC$_6$H$_5$ there is produced 5-methyl-10,11-dihydro-5H-dibenzo-[a,d]cyclohepten-5,10-imine identical with previously prepared material in substantially similar yields in accordance with the following reaction scheme:

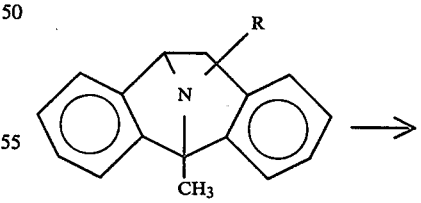

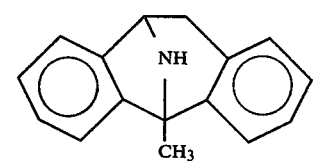

Employing the procedure substantially as described in Example 1, Steps A through D but substituting for the hydroxylamine used in Step B thereof, equimolecular amounts of amines of the formula NH₂R, there are produced in sequence the intermediates:

5-methyl-5-(R-amino)-5H-dibenzo[a,d]cycloheptene (3);

12-R-5-methyl-10,11-dihydro-5H-dibenzo[a,d]cyclohepten-5,10-imine (4) and finally 5-methyl-10,11-dihydro-5H-dibenzo[a,d]cyclohepten-5,10-imine (5)

wherein R is:

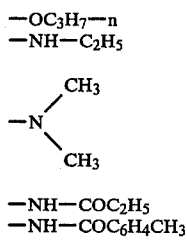

—OC₃H₇—n
—NH—C₂H₅
—N(CH₃)(CH₃)
—NH—COC₂H₅
—NH—COC₆H₄CH₃

Step A:
5-Methyl-5H—dibenzo[a,d]cyclohepten-5-ol (2)

See Example 1, Step A.

Step B:
5-Methyl-5-azido-5H—dibenzo[a,d]cycloheptene (6)

| Carbinol (1) | 10.0 g | 4.5 × 10⁻² mol |
|---|---|---|
| NaN₃ | 11.6 g | 1.78 × 10⁻¹ mol |
| CF₃CO₂H | 18.0 mls | 2.11 × 10⁻¹ mol |

In a 3-necked flask was placed 11.6 g (1.78×10⁻¹ mol) NaN₃ in 0.25 l of CH₂Cl₂ under N₂. To this was added with cooling (0° C.) 18.0 ml (2.11×10⁻¹ mol) CF₃CO₂H over 5 minutes. The reaction was stirred for 10 minutes at room temperature and 10.0 g (4.5×10⁻² mol) of carbinol in 0.1 l of CH₂Cl₂ was added dropwise (15 minutes) at ambient temperature. After 40 minutes, 0.100 l of ice water and 25 ml of concentrated NH₄OH was added (pH>8) and the reaction was stirred for 10 minutes. The organic layer was separated and the aqueous layer extracted with 1×30 ml of CH₂Cl₂. The organic layers were combined, washed with 1×100 ml of brine, dried with MgSO₄ and the solvent was removed under reduced pressure to give 11.0 g crystalline product, 6, (97%).

m.p. 65.5° C.–67° C.

¹HNMR (CDCl₃)δ1.90 (s, 3H, CH₃), 6.95 (s, 2H, HC=CH) and 7.00–7.80 (m, 8H, Ar) IR (CDCl₃) 2125 cm⁻¹(N₃).

Step C:
5-Methyl-5-Amino-5H—dibenzo[a,d]cycloheptane, (7)

| Azide (6) | 7.0 g | 2.83 × 10⁻² mol |
|---|---|---|
| PtO₂ | 1.4 g | |
| Absolute Ethanol | 210 ml. | |

7.0 g (2.83×10⁻² mol) of 6 dissolved in 0.21 l of absolute ethanol was charged with 1.4 g PtO₂ and placed on a Parr shaker overnight under H₂ at 5 psi and ambient temperature. The mixture was filtered through Super-Cel, and the filtrate stripped of solvent. The resulting oil was taken up in 50 ml of CH₂Cl₂ and extracted with 3×25 ml of 10% HCl. The aqueous layers were combined, basified with concentrated NH₄OH, extracted with 3×25 ml of CH₂Cl₂. The organic layers were combined, dried with MgSO₄ and the solvent removed to give 3.85 g of the desired amine 7 in a 62% yield.

¹HNMR (CDCl₃)δ1.77 (s, 3H, CH₃), 2.10 (s, 2H, NH₂ exchanged by D₂O), 7.00 (s, 2H, HC=CH) and 7.05–7.75 (m, 8H, Ar).

IR (neat) 3300–3400 (broad NH₂), 1580, 1430 and 1475 cm⁻¹.

Step D:
(±)-5-Methyl-10,11-dihydro-5H—dibenzo[a,d]cyclohepten-5,10-imine (5)

| Amine (7) | 0.5 g | 2.26 × 10⁻³ mol |
|---|---|---|
| KOtBu | 0.26 g | 2.26 × 10⁻³ mol |
| DMSO | 5.0 ml | |

0.26 g (2.26×10⁻³ mol) KOt-Bu was placed in 2.5 ml of sieve dried DMSO under N₂ and warmed to 75° C. To this was added dropwise 0.5 g (2.26×10⁻³ mol) of amine 7 dissolved in 2.5 ml of DMSO. The reaction was heated at 125° C. for approximately 18 hours. The reaction was cooled to ambient temperature and 10 ml of H₂O, and 10 ml of ethyl acetate added and the reaction mixture was stirred open to the air. The aqueous layer was separated and back washed with 5 ml of ethyl acetate. The original ethyl acetate layer was washed with 2×10 ml of H₂O. The ethyl acetate back-wash was then extracted with these two 10 ml H₂O washes. Both organic layers were combined and washed with 1×10 ml of brine, dried over MgSO₄ and stripped of solvent to give 0.4 g of 5 in 80% yield.

OPTICAL RESOLUTION
Preparation of (+)-5-Methyl-10,11-dihydro-5H—dibenzo[a,d]cyclohepten-5,10-imine.di-p-toluoyl-l-tartaric acid.acetone.

Materials:

| (±)-5-Methyl-10,11-dihydro-5H—dibenzo[a,d]cyclohepten-5,10-imine (5) | 284.4 g | 1.29 mol |
|---|---|---|
| Di-p-toluoyl-l-tartaric acid-monohydrate | 720 g | 1.78 mol |
| Acetone | 3.25 l. | |
| Methylene chloride | 6.0 l. | |
| Concentrated ammonium hydroxide | 1.5 l. | |

The cyclic amine 5 (284.4 g, 1.29 mol) was dissolved in 402 ml of acetone and filtered through a medium sintered glass funnel into a 3-l. 3-necked flask fitted with a mechanical stirrer and thermometer. An additional 63 ml of acetone was used as a rinse.

A solution of 519 g (1.28 mol) of the resolving acid in approximately 600 ml of warm acetone was similarly filtered into a separate flask with an additional 60 ml used for rinsing. The amine solution was warmed to 40° C. and the resolving acid solution added rapidly with stirring (T₁ approximately 40° C.). The solution was seeded and the reaction mixture brought to ambient temperature with stirring overnight.

The mixture was filtered and the white, finely crystalline product washed with 4×200 ml cold acetone (10° C.) and air dried at 55° C. to give 331 g (0.497 mol; 39%) of diastereomeric salt [α]_D²⁵=127.7° (C=1, abs. ethanol).

A solution of 330 g of the enriched salt in 3.0 l. of methylene chloride was added to 6.0 l. of 1:3 concentrated ammonium hydroxide/H₂O (v/v) and stirred. The CH₂Cl₂ layer was separated and the basic layer extracted with 2×1.5 l. of CH₂Cl₂. The organic layers were combined, dried over MgSO₄, filtered and concentrated to a viscous oil (119.6 g).

The viscous oil was dissolved in 254 ml of acetone and filtered into a 3 l. 3-neck flask as previously described, using 208 ml of acetone as a rinse. A solution of 200.7 g (0.497 mol) of resolving acid dissolved in 254 ml of acetone was filtered as described previously, using 208 ml acetone as a rinse and added to the amine solution at 42°–43° C. The reaction mixture was seeded and brought to ambient temperature with stirring overnight. The white precipitate was filtered, washed with 4×100 ml of cold acetone (10° C.) and air dried at 50° to 60° C. to give 294.2 g (89%) of crystalline salt m.p. 137°–138° C. (dec); $[\alpha]_D^{25} = +132.2°$ (C=1, abs. ethanol).

| Preparation of (+)-5-Methyl-10,11-dihydro-5H— dibenzo[a,d]cyclohepten-5,10-imine.hydrogen maleate | | |
|---|---|---|
| Materials: | | |
| (+)-5-Methyl-10,11-dihydro-5H— dibenzo[a,d]cyclohepten-5,10-imine.di-p-toluoyl-l-tartaric acid.acetone | 293 g | 0.44 mol |
| Methylene chloride | 5.4 l. | |
| Concentrated ammonium hydroxide | 1.3 l. | |
| Maleic acid (Aldrich) | 51.07 g | 0.44 mol |
| Absolute ethanol | 1.05 l. | |

The amine salt, 293 g (0.44 mol) was dissolved in 2.7 l. CH₂Cl₂ to which 5.2 l. of 1:3 concentrated ammonium hydroxide/H₂O was added. The basic layer was separated, washed with 2×1.35 l. CH₂Cl₂, the organic layers combined, dried over MgSO₄, filtered and concentrated under reduced pressure to a viscous oil (105 g).

The viscous oil was dissolved in 282 ml of absolute ethanol and filtered through a medium sintered-glass funnel into a 2-l. 3-necked flask fitted with a mechanical stirrer and thermometer, using an additional 145 ml of absolute ethanol as a rinse.

A solution of 51.07 g (0.44 mol) of maleic acid dissolved in 141 ml of absolute ethanol was filtered as previously described using 78 ml of absolute ethanol as a rinse and added rapidly with stirring to the warmed amine solution (44° C.).

The reaction mixture was stirred for 10 minutes (T$_i$ 47° C.), seeded and slowly stirred overnight at room temperature. The white precipitate was filtered, washed with 4×100 ml cold absolute ethanol (5° C.) and dried under vacuum at 50°–60° C. to give 129.1 g (87%) of crystalline (+)-5-methyl-10,11-dihydro-5H-dibenzo[a,d]cyclohepten-5,10-imine.hydrogen maleate m.p. 205.5°–206.,5° C.(d) with an observed rotation of $[\alpha]_D^{25} = +114.7$ (C=1, methanol).

What is claimed is:

1. A process for the preparation of the racemic compound of structural formula:

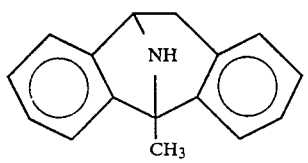

which comprises the steps of:
(a) reacting a compound of structural formula:

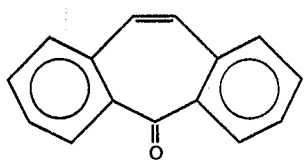

with a methylmagnesium halide in an ethereal solvent at −50+ to +50° C. to produce the carbinol of structural formula 2 and isolating compound 2:

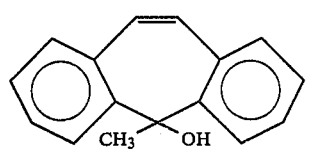

(b) reacting 2 with a substituted amine of formula NH₂-R, and an intermediate strength organic acid in a chlorinated C₁₋₃alkane at −20 to +50° C. to produce the substituted amino compound of structural formula 3 and isolating compound 3:

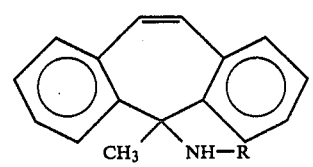

wherein R is —OR¹ wherein R¹ is hydrogen or C₁₋₃alkyl, or R is —NR²R³ wherein R² and R³ are independently hydrogen, C₁₋₃alkyl, C₂₋₃alkanoyl, or benzenoid aroyl, or R² and R³ taken together represent tetramethylene or pentamethylene, (c) reacting 3 with a strong base selected from the group consisting of an alkali metal hydride, amide or alkoxide, in a benzenoid aromatic solvent, dimethylsulfoxide, dimethylformamide or mixtures thereof at 0° to 190° C., to produce the compound of structural formula 4 and isolating compound 4:

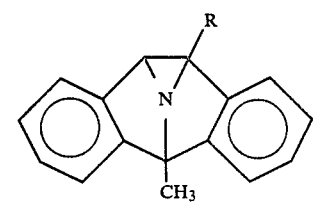

(d) reacting 4 with hydrogen in a solvent in the presence of a noble metal catalyst and isolating compound 5.

2. The process of claim 1 for the preparation of the racemic compound of structure:

which comprises the steps of:
(a) reacting a compound of structural formula:

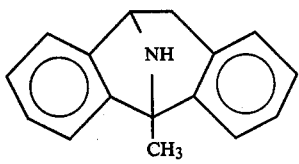

which comprises the steps of:
(a) reacting a compound of structural formula:

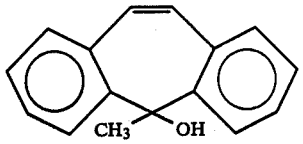

with a substituted amine of formula NH$_2$-R and an intermediate strength organic acid in a chlorinated C$_{1-3}$alkane at $-20°$ to $+50°$ C. to produce the substituted amino compound of structural formula 3 and isolating compound 3:

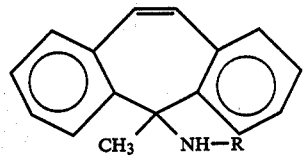

wherein R is —OR$^1$ wherein R$^1$ is hydrogen or C$_{1-3}$alkyl, or R is —NR$^2$R$^3$ wherein R$^2$ and R$^3$ are independently hydrogen, C$_{1-3}$alkyl, C$_{2-3}$alkanoyl, or benzenoid aroyl, or R$^2$ and R$^3$ taken together represent tetramethylene or pentamethylene,
(b) reacting 3 with a strong base selected from the group consisting of an alkali metal hydride, amide or alkoxide, in a benzenoid aromatic solvent, dimethylsulfoxide, dimethylformamide or mixtures thereof at 0° to 190° C., to produce the compound of structural formula 4 and isolating compound 4:

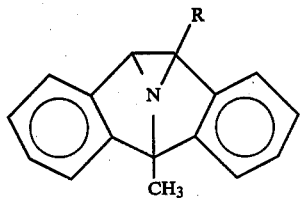

(c) reacting 4 with hydrogen in a solvent in the presence of a noble metal catalyst and isolating compound 5.

3. The process of claim 1 for the preparation of the racemic compound of structural formula:

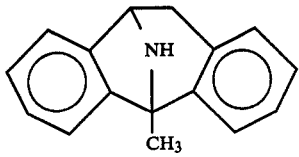

which comprises the steps of:
(a) reacting a compound of structural formula:

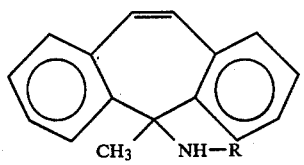

with a strong base selected from the group consisting of an alkali metal hydride, amide or alkoxide, in a benzenoid aromatic solvent, dimethylsulfoxide, dimethylformamide or mixtures thereof at 0° to 190° C., to produce the compound of structural formula 4 and isolating compound 4:

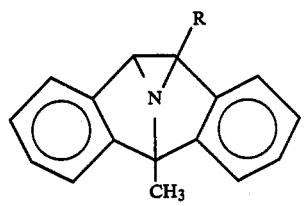

wherein R is —OR$^1$ wherein R$^1$ is hydrogen or C$_{1-3}$alkyl, or R is —NR$^2$R$^3$ wherein R$^2$ and R$^3$ are independently hydrogen, C$_{1-3}$alkyl, C$_{2-3}$alkanoyl, or benzenoid aroyl, or R$^2$ and R$^3$ taken together represent tetramethylene or pentamethylene,
(b) reacting 4 with hydrogen in a solvent in the presence of a noble metal catalyst and isolating compound 5.

4. The process of claim 1, 2 or 3 wherein R is —OH, —OCH$_3$, —NH$_2$ or —NHCOC$_6$H$_5$.

5. The process of claim 1, 2 or 3 wherein R is —OH.

6. A process for the preparation of the racemic compound of structural formula:

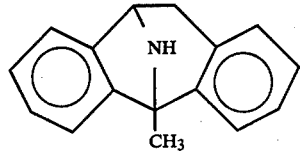

which comprises the steps of:
(a) reacting a compound of structural formula:

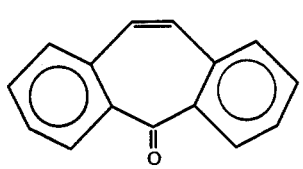

with a methylmagnesium halide in an ethereal solvent at $-50°$ to $+50°$ C. to produce the carbinol of structural formula 2 and isolating compound 2:

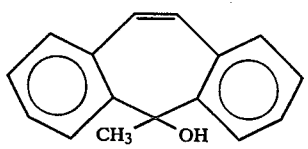

2

(b) reacting 2 with sodium azide and an organic acid in a chlorinated $C_{1-3}$alkane at $-20°$ to $+50°$ C. to produce the compound of structural formula 6 and isolating compound 6:

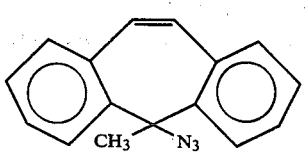

6

(c) reacting 6 with hydrogen in a solvent in the presence of a noble metal catalyst to produce the compound of formula 7 and isolating compound 7:

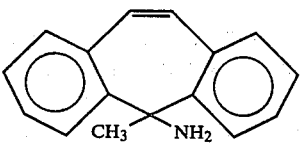

7

(d) reacting 7 with a strong base selected from the group consisting of an alkali metal hydride, amide or alkoxide, in a benzenoid aromatic solvent, dimethylsulfoxide, dimethylformamide or mixtures thereof at 0° to 190° C. and isolating compound 5.

7. The process of claim 1 for the preparation of the racemic compound of structure:

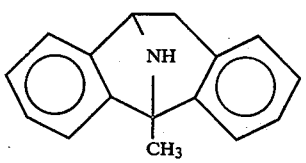

5 which comprises the steps of:
(a) reacting a compound of structural formula:

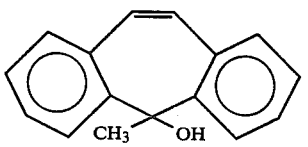

2 with sodium azide and an organic acid in a chlorinated $C_{1-3}$alkane at $-20°$ to $+50°$ C. to produce the compound of structural formula 6 and isolating compound 6:

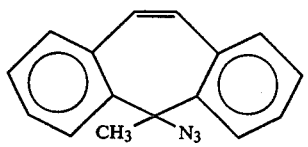

6

(b) reacting 6 with hydrogen in a solvent in the presence of a noble metal catalyst to produce the compound of structure 7 and isolation of compound 7;

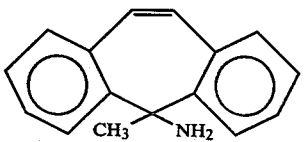

7

(c) reacting 7 with a strong base selected from the group consisting of an alkali metal hydride, amide or alkoxide, in a benzenoid aromatic solvent, dimethylsulfoxide, dimethylformamide or mixtures thereof at 0° to 190° C. and isolating compound 5.

8. The process of claim 6 for the preparation of the racemic compound of structural formula:

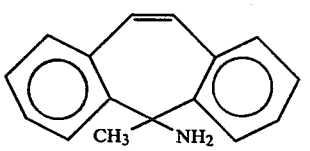

5 which comprises the steps of:
(a) reacting a compound of structural formula:

6 with hydrogen in a solvent in the presence of a noble metal catalyst to produce the compound of structural formula 7 and isolating compound 7:

7

(b) reacting a compound of structural formula:

7 with a strong base selected from the group consisting of an alkali metal hydride, amide or alkoxide, in a benzenoid aromatic solvent, dimethylsulfoxide, dimethylformamide or mixtures thereof at 0° to 190° C. and isolating compound 5.

9. The process of claim 6 for the preparation of the racemic compound of structural formula:

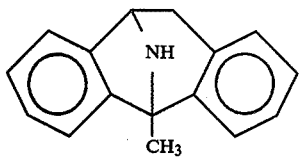

5 which comprises reacting the compound of structural formula:

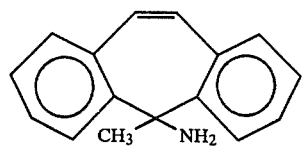

7 with a strong base selected from the group consisting of an alkali metal hydride, amide or alkoxide, in a benzenoid aromatic solvent, dimethylsulfoxide, dimethylformamide or mixtures thereof at 0° to 190° C. and isolating compound 5.

* * * * *